Figure 2:
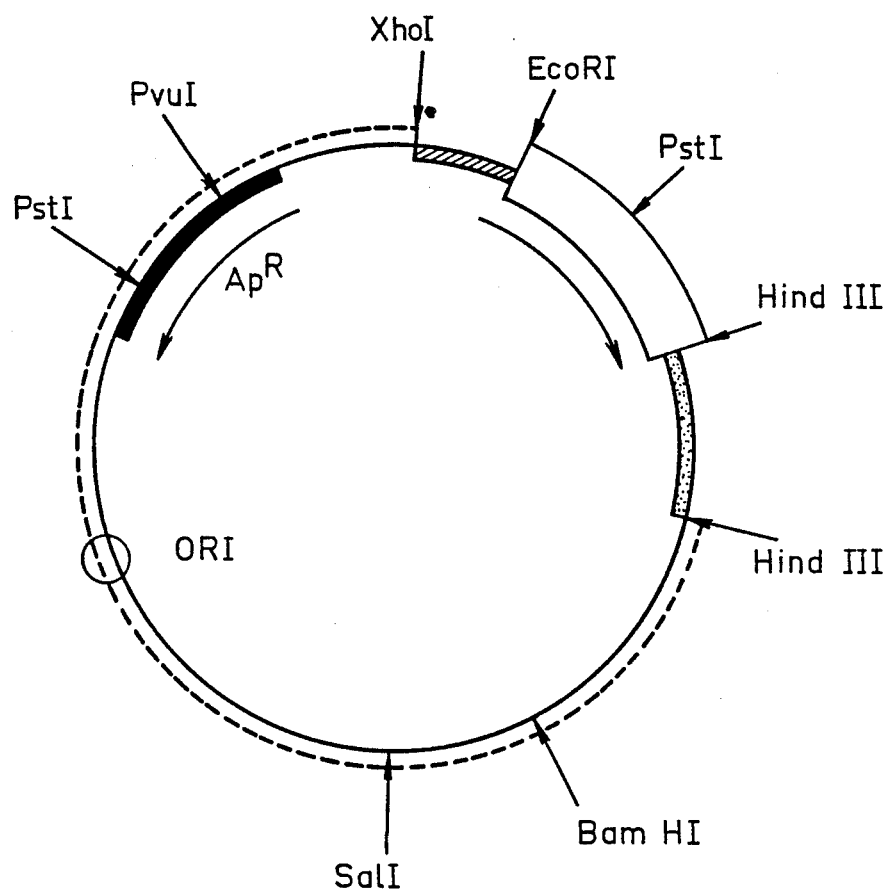

United States Patent [19]

Legoux et al.

[11] Patent Number: 4,945,047

[45] Date of Patent: Jul. 31, 1990

[54] MICROBIOLOGICAL PROCESS FOR THE PREPARATION OF A PROTEIN BY CULTURING A MUTANT BACTERIAL STRAIN

[75] Inventors: Richard Legoux, Caraman; Pascal Leplatois, Cuq Toulsa; Evelyne L. Joseph, Saint Orens De Gameville; Brigitte Niaudet, Toulouse; Willem Roskam, Montgiscard, all of France

[73] Assignee: Societe Anonyme: Sanofi, Paris, France

[21] Appl. No.: 36,263

[22] Filed: Apr. 9, 1987

[30] Foreign Application Priority Data

Apr. 10, 1986 [FR] France ............................... 86 05133

[51] Int. Cl.$^5$ .................. C12P 21/00; C12N 15/00; C12R 1/07; C12R 1/185
[52] U.S. Cl. .................. 435/69.4; 435/172.3; 435/252.3; 435/252.33; 435/172.1; 435/69.8; 935/41; 935/56; 935/60; 935/73; 935/61
[58] Field of Search ............ 435/68, 172.3, 253, 435/320, 172.1, 252.1, 252.33, 252.3, 252.8

[56] References Cited

PUBLICATIONS

Dunlap et al., 1985, J. Bacteriol., 164(1):45–50.
Amann et al., 1983, Gene, 25:167–178.
J. Daniel; Fems Microbiology Letters, vol. 24, 1984, pp. 215–218.
G. L. Gray et al.; Gene, vol. 39, No. 2/3, 1985, pp. 247–254.
R. Utsumi; Agricultural and Biological Chemistry, vol. 48, No. 8, 1984, pp. 2129–2130.
A. H. Koop et al.; Gene, vol. 28, 1984, pp. 133–146.

Primary Examiner—Charles F. Warren
Assistant Examiner—David T. Fox
Attorney, Agent, or Firm—Davis, Hoxie, Faithfull & Hapgood

[57] ABSTRACT

The invention relates to a microbiological process for the preparation of a protein by culturing a mutant bacterial strain.

This process consists in using a bacterial strain carrying a mutation which limits, or even suppresses, the expression of the operons whose transcription depends on the fixation of the cAMP-CRP complex, a DNA sequence coding for a protein precursor having been introduced into the said bacterial strain.

15 Claims, 3 Drawing Sheets

Fig. 1

```
5' ATG GCT ACA GGC TCC CGG ACG TCC CTG CTC CTG GCT TTT GGC CTG CTC TGC CTG
   TAC CGA TGT CCG AGG GCC TGC AGG GAC GAG GAC CGA AAA CCG GAC GAG ACG GAC
   M   A   T   G   S   R   T   S   L   L   L   A   F   G   L   L   C   L
   -26
   CCC TGG CTT CAA GAG GGC AGT GCC TTC CCA ACC ATT CCC TTA TCC AGG CTT TTT
   GGG ACC GAA GTT CTC CCG TCA CGG AAG GGT TGG TAA GGG AAT AGG TCC GAA AAA
   P   W   L   Q   E   G   S   A   F   P   T   I   P   L   S   R   L   F
                                   1                                    10
   GAC AAC GCT ATG CTC CGC GCC CAT CGT CTG CAC CAG CTG GCC TTT GAC ACC TAC
   CTG TTG CGA TAC GAG GCG CGG GTA GCA GAC GTG GTC GAC CGG AAA CTG TGG ATG
   D   N   A   M   L   R   A   H   R   L   H   Q   L   A   F   L   T   Y
                                           20
   CAG GAG TTT GAA GAA GCC TAT ATC CCA AAG GAA CAG AAG TAT TCA TTC CTG CAG
   GTC CTC AAA CTT CTT CGG ATA TAG GGT TTC CTT GTC TTC ATA AGT AAG GAC GTC
   Q   E   F   E   E   A   Y   I   P   K   E   Q   K   Y   S   F   L   Q
       30                                      40
   AAC CCC CAG ACC TCC CTC TGT TTC TCA GAG TCT ATT CCG ACA CCC TCC AAC AGG
   TTG GGG GTC TGG AGG GAG ACA AAG AGT CTC AGA TAA GGC TGT GGG AGG TTG TCC
   N   P   Q   T   S   L   C   F   S   E   S   I   P   T   P   S   N   R
                   50                                  60
   GAG GAA ACA CAA CAG AAA TCC AAC CTA GAG CTG CTC CGC ATC TCC CTG CTG CTC
   CTC CTT TGT GTT GTC TTT AGG TTG GAT CTC GAC GAG GCG TAG AGG GAC GAC GAG
   E   E   T   Q   Q   K   S   N   L   E   L   L   R   I   S   L   L   L
                           70                                  80
   ATC CAG TCG TGG CTG GAG CCC GTG CAG TCC CTC AGG AGT GTC TTC GCC AAC AGC
   TAG GTC AGC ACC GAC CTC GGG CAC GTC AAG GAG TCC TCA CAG AAG CGG TTG TCG
   I   Q   S   W   L   E   P   V   Q   F   L   R   S   V   F   A   N   S
                                   90                                  100
   CTG GTG TAC GGC GCC TCT GAC AGC AAC GTC TAT GAC CTC CTA AAG GAC CTA GAG
   GAC CAC ATG CCG CGG AGA CTG TCG TTG CAG ATA CTG GAG GAT TTC CTG GAT CTC
   L   V   Y   G   A   S   D   S   N   V   Y   D   L   L   K   D   L   E
                                       110
   GAA GGC ATC CAA ACG CTG ATG GGG AGG CTG GAA GAT GGC AGC CCC CGG ACT GGG
   CTT CCG TAG GTT TGC GAC TAC CCC TCC GAC CTT CTA CCG TCG GGG GCC TGA CCC
   E   G   I   Q   T   L   M   G   R   L   E   D   G   S   P   R   T   G
       120                                         130
   CAG ATC TTC AAG CAG ACC TAC AGC AAG TTC GAC ACA AAC TCA CAC AAC GAT GAC
   GTC TAG AAG TTC GTC TGG ATG TCG TTC AAG CTG TGT TTG AGT GTG TTG CTA CTG
   Q   I   F   K   Q   T   Y   S   K   F   D   T   N   S   H   N   D   D
               140                                         150
   GCA CTA CTC AAG AAC TAC GGG CTG CTC TAC TGC TTC AGG AAG GAC ATG GAC AAG
   CGT GAT GAG TTC TTG ATG CCC GAC GAG ATG ACG AAG TCC TTC CTG TAC CTG TTC
   A   L   L   K   N   Y   G   L   L   Y   C   F   R   K   D   M   D   K
                           160                                 170
   GTC GAG ACA TTC CTG CGC ATC GTG CAG TGC CGC TCT GTG GAG GGC AGC TGT GGC
   CAG CTC TGT AAG GAC GCG TAG CAC GTC ACG GCG AGA CAC CTC CCG TCG ACA CCG
   V   E   T   F   L   R   I   V   Q   C   R   S   V   E   G   S   C   G
                                   180
   TTC 3'
   AAG
   F
   191
```

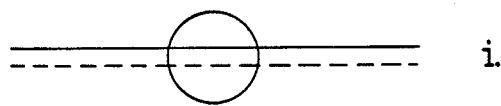 i.
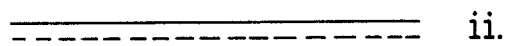 ii.
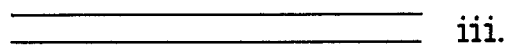 iii.
 iv.
 v.
 vi.
Fig. 2a
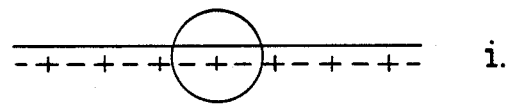 i.
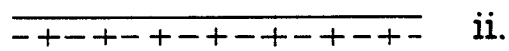 ii.
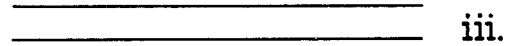 iii.
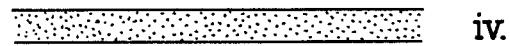 iv.
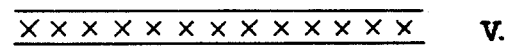 v.
 vi.
 vii.
Fig. 3a

MICROBIOLOGICAL PROCESS FOR THE PREPARATION OF A PROTEIN BY CULTURING A MUTANT BACTERIAL STRAIN

The present invention relates to a microbiological process which makes it possible to obtain a protein by culturing Gram-negative bacteria carrying a mutation of a particular type, a DNA sequence coding for the precursor of the said protein having been introduced into the said bacteria.

The invention can be applied in numerous technical fields and more particularly in the preparation of drugs in which the active principle is a protein.

It is known that numerous proteins only acquire their biological activity after they have been subjected to post-translational maturation. In the case of proteins biosynthesized in the cytoplasm in the form of a precursor and then exported out of the cytoplasm, the first step of this maturation is often the enzymatic elimination of a sequence of the N-terminal end, called a signal peptide, from this precursor. Proteins of this type, biosynthesized in the form of a precursor, are known both in prokaryotic organisms and in eukaryotic organisms. Examples of such proteins which may be mentioned in particular are beta-lactamase TEM-1 and alkaline phosphatase, both of which are produced for example by the species *Escherichia coli*, protein A produced by the species *Staphylococcus aureus*, and alphaamylase produced for example by the species *Bacillus amyloliquefaciens*, these being proteins of prokaryotic origin, and also human growth hormone, human insulin, tissue plasminogen activator and epidermal growth factor, these proteins being produced by eukaryotic cells.

It is also known that it is possible to use Gram-negative bacteria, which have first been transformed by a plasmid carrying a DNA sequence coding for the natural precursor of a protein, in order to prepare the said protein (G. L. Gray et al., Biotechnology 2 (1984) 161–165; G. L. Gray et al., Gene 39 (1985) 247–254). In such a case, the cell machinery ensures that, in the cytoplasmic compartment, the DNA sequence is transcribed and the corresponding messenger RNA is then translated; during or after transfer across the cytoplasmic membrane, the precursor biosynthesized in this way then undergoes enzymatic cleavage or degradation, eliminating its signal peptide; the protein, which thus corresponds to the precursor without its signal peptide, accumulates in the periplasm of the bacterium, from which it can be collected.

Analogous results have also been obtained when the said DNA sequence codes for a precursor differing from the natural precursor (i.e. in the form in which it is synthesized in the cells which normally produce it) as regards the signal peptide; for example, a precursor corresponding to a protein of eukaryotic origin associated with the signal peptide of a protein of bacterial origin has been synthesized (K. Talmadge et al., Proc. Natl. Acad. Sci. U.S.A., 77 (1980) 3988–3992; G. L. Gray et al., Gene 39 (1985) 247–254).

It is also known that bacteria can be subject to mutations which limit, or even suppress, the expression of operons whose transcription can only be initiated after fixation, to the regulator elements of the said operons, of the cAMP-CRP complex resulting from association of the adenosine 3′,5′-cyclic phosphoric acid (or cAMP) with the CRP (cyclic AMP receptor protein), which is also called CAP (catabolite activator protein). A description of how these operons function is given in the chapter "The Lac Promoter—W.S. REZNIKOFF and J.N. ABELSON" of the work "The Operon—J. H. MILLER and W.S. REZNIKOFF, Cold Spring Harbor Laboratory—1980".

It is clear that such bacteria, which have a reduced ability to biosynthesize (because the operons inhibited here govern the synthesis of numerous enzymes), were a priori unable to form preferred hosts for the industrial production of a protein.

The work published by G. L. Gray et al. in 1984 and 1985 (see above) shows that the research hitherto undertaken to prepare a protein, by culturing bacteria into which a DNA sequence coding for a precursor of the said protein has been introduced, have been directed towards the construction of plasmids rendered more efficient by a particular choice of regulator elements (especially promoters).

The Applicants in fact chose another line of research by taking an interest in the bacterial host. This is how it found, surprisingly, that Gram-negative bacteria whose chromosome carries at least one mutation which limits, or even suppresses, the expression of operons whose transcription depends on the fixation of the cAMP-CRP complex constitute preferred hosts for the industrial production of proteins biosynthesized in the form of a precursor.

According to a first feature, the present invention therefore relates to a microbiological process for the preparation of a protein by culturing Gram-negative bacteria into which a DNA sequence coding for a precursor of this protein has been introduced, which comprises using a strain of bacteria whose chromosome carries at least one mutation which limits, or even suppresses, the expression of the operons whose transcription depends on the fixation of the cAMP-CRP complex.

The mutations in question are those which tend to reduce the intracellular concentration of cAMP, those which limit or suppress the synthesis of CRP in a functional form, those which lead to the synthesis of CRP in a mutated form and result in the formation of cAMP-CRP complexes which are such that their fixation to the DNA is prevented or rendered relatively inefficient, and also those which modify the site of fixation of the cAMP-CRP complex to the DNA in such a way that the fixation of the said complex is prevented or rendered relatively inefficient. They can be conditional mutations whose expression depends on a parameter such as, for example, temperature.

Among these mutations, those which affect the chromosomal gene cya itself, or a DNA sequence regulating its expression, in such a way that the adenylate cyclase for which this gene codes is not synthesized or is synthesized in a form such that it is incapable of exerting its specific activity—namely the transformation of adenosine triphosphate (or ATP) to cAMP—are well characterized. The same applies to the mutations which affect the chromosomal gene crp itself, or a DNA sequence regulating its expression, in such a way that the CRP for which this gene codes is not synthesized or is synthesized in a mutated form which is such that there cannot be any formation of cAMP-CRP complexes which are sufficiently stable to permit their efficient fixation to the DNA. For convenience, these mutations will be designated hereafter as cya mutation and crp mutation.

The cya and cro mutations can be of any kind: particular possibilities are a mutation by substitution, a mutation by insertion, a mutation by inversion or, for example, a mutation by deletion. The mutation may affect only a single pair of nucleotides, but as a point mutation of this type is reversible, preference is given to a mutation simultaneously affecting several pairs of nucleotides, which is irreversible. Multiple point mutations are a further possibility. In the case of a cya mutation, cAMP is not synthesized and formation of the cAMP-CRP complex cannot take place; the addition of exogenous cAMP makes it possible to overcome this synthesis defect and restores the perturbed cell functions. In the case of a crp mutation, CRP is no longer synthesized in a functional form and, again, formation of the cAMP-CRP complex cannot take place; this time, the addition of exogenous cAMP is powerless to restore the perturbed cell functions.

The invention advantageously relates to the microbiological process defined above which uses a strain of bacteria whose chromosome carries at least one mutation affecting the system formed by the cya gene and the DNA sequences regulating its expression, the system formed by the crp gene and the DNA sequences regulating its expression, or alternatively both these systems.

The bacterial strains used according to the invention can belong to any Gram-negative species in which the cAMP coupled to the CRP exerts control over the expression of various operons. The use of bacterial strains of this type for industrial production is all the more advantageous because they have a remarkable resistance to the action of numerous bacteriophages (Sushil Kumar, J. Bact. 125 (1976) 545-555). A preferred species is *Escherichia coli*.

According to another feature, the invention relates to the said microbiological process wherein the mutant bacterial strain used is a strain of the species *Escherichia coli*.

The Applicant Company selected, more particularly, two mutant strains of *Escherichia coli* deposited on 17 February 1986 in the National Collection of Microorganism Cultures (C.N.C.M., Paris, France). One of the strains carries a point crp mutation (deposit no. I-528); the other strain carries a non-point cya mutation by deletion (deposit no. I-529).

The invention preferentially relates to the said microbiological process wherein the mutant strain has the characteristics of one or other of the strains deposited in the C.N.C.M. under no. I-528 and I-529.

The process of the invention makes it possible to obtain numerous proteins. It must be understood that it is of little importance whether or not the protein which it is desired to prepare is naturally or not biosynthesized in the form of a precursor. The process is also suitable for the preparation of an unnatural protein; for example, this can be a hybrid protein whose primary structure has been selected from two or more known proteins. In all cases, it suffices to prepare a DNA sequence coding for the said protein associated at its N-terminal end with a peptide behaving as a signal peptide.

The process according to the invention is particularly advantageous for the preparation of human growth hormone (designated hereafter by the symbol hGH in the text).

FIG. 1 shows the DNA sequence coding for one of the natural precursors of hGH, as isolated from the pituitary gland cells where it is synthesized, and also the amino acid sequence of the said precursor: the first 26 amino acids (counted in the figure starting from the amino acid in the −26position) constitute the signal peptide and the other 191 amino acids (numbered here from 1 to 191) are those of the actual hGH (referred to hereafter as "mature hGH" in the text and the examples).

Table no. 1 below is inserted here in order to provide a better understanding of FIG. 1, where each of the amino acids is represented by a single letter.

TABLE NO. 1

| Amino acid | Letter |
| --- | --- |
| Alanine | A |
| Arginine | R |
| Asparagine | N |
| Aspartic acid | D |
| Cysteine | C |
| Glutamine | Q |
| Glutamic acid | E |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

In the codons of the DNA sequence represented in FIG. 1, the letters A, C, T and G have the usual meanings and respectively denote the following bases: adenine, cytosine, thymine and guanine.

To be implemented, the invention requires that mutant bacteria include a DNA sequence coding for the precursor of the desired protein. The term "precursor" is understood as meaning the natural precursor of the protein, if it exists, any derivative of the said natural precursor obtained by modification of its signal peptide, and any precursor which associates, with the said protein, a peptide which is capable of behaving as a signal peptide and can be selected in particular from the group comprising the known prokaryotic and eukaryotic signal peptides or their derivatives.

The DNA sequence coding for the precursor of the said protein can be introduced into the bacterium carried by an expression vector capable of replication, such as a plasmid. It is clear that the regulator elements (especially promoter) necessary for expression of the said sequence must be located in its vicinity so that they can perform their function.

Examples of plasmids which can be used are those described in the prior art (G. L. Gray et al., Gene 39 (1985) 247-254), provided they are capable of replicating in the bacterial strain used. As regards the choice of these plasmids, it has been shown that, in the construction used, the DNA sequence coding for the precursor of the desired protein does not have to be inducible. It is also important for the said sequence to be present in several copies.

The Applicants in fact constructed and selected several plasmids capable of being present, after replication in the bacterial cells, in a proportion of 50 to 300 copies per cell, each copy carrying a copy of the DNA sequence coding for the precursor of the desired protein; on Feb. 17, 1986, the strain *E. coli MC* 1061 transformed by one of these plasmids was deposited in the C.N.C.M.; this strain has the deposit no. I-530. For convenience, we will refer in the remainder of the description to the plasmid deposited in the C.N.C.M. under no. I-530. This plasmid, which is also denoted hereafter by its internal reference p163,1, carries a DNA sequence coding for one of the natural precursors of hGH. This sequence, shown in FIG. 1, is identical to that determined from one of the precursors synthesized in human pituitary gland cells; it was placed under the control of a hybrid promoter-operator associating (1) a fragment of the tryptophan promoter starting from its 5,40 -end and including its RNA polymerase recognition site (site centred on its nucleotide located in the -35 position and as defined by M. Takanami et al., Nature 260 (1976) 297-302), and (2) the promoter-operator lactose UV5 without the part between its 5'-end and the region separating its RNA polymerase recognition site (site centered on its nucleotide located in the -35 position) and fixation site (site centered on its nucleotide located in the −10 position and as defined by D. Pribnow, Proc. Natl. Acad. Sci. U.S.A. 72 (1975) 784–789).

FIG. 2 shows, for the said plasmid, a functional map indicating the location and orientation of the main DNA sequences, which are represented symbolically according to the following legend, as depicted in FIG. 2a:

i Origin of replication (ORI)
ii. DNA segment originating from the plasmid pBR322
iii. DNA segment containing the sequence coding for the natural precursor of hGH
iv. DNA segment of the phage fd containing a transcription terminator
v. DNA segment containing the hybrid promoter-operator tryptophan-lactose UV5.
vi. DNA segment coding for β-lactamase (ApR: ampicillin resistance)

This map also shows the action sites of certain restriction enzymes, namely the enzymes SalI, BamHI, HindIII, PstI, EcoRI, XhoI and PvuI.

The presence, in the plasmid p163,1, of the mutation UV5 (described in the chapter "The Lac Promoter, W.S. REZNIKOFF and J.N. ABELSON" of the work "The Operon, Cold Spring Harbor Laboratory, 1980") renders the expression of the DNA sequence coding for the precursor of hGH insensitive to the combined action of cAMP and CRP. It is clear that this plasmid can be used to construct other plasmids, assuming its general characteristics, by substitution, for the DNA sequence coding for one of the natural precursors of hGH, of a sequence coding for another precursor, especially for a precursor of another protein.

According to another feature, the invention relates to the said microbiological process wherein the DNA sequence coding for the precursor of the desired protein, accompanied by the regulator elements permitting its expression, is carried by a plasmid; it relates in particular to the said microbiological process wherein the said DNA sequence is carried by a plasmid having the general characteristics of the plasmid deposited in the C.N.C.M. under no. I-530.

According to another feature, the invention relates to the said microbiological process wherein the said bacterial strain contains a DNA sequence coding for the precursor of hGH.

According to another feature, the invention relates to the bacterial strains deposited in the C.N.C.M. under no. I-528 and I-529.

According to yet another feature, the invention relates to the plasmid deposited in the C.N.C.M. under no. I-530.

The invention will no be illustrated by means of examples. Of course, it is not limited to the methods of application considered more particularly in these examples; on the contrary, it encompasses all the variants thereof within the scope of the claims.

EXAMPLES

I. Bacteria and plasmids used

Four bacterial strains and four plasmids were used.

Apart from the strains deposited in the C.N.C.M. under no. I-528 and I-529, two other strains of *Escherichia coli* are mentioned in the examples:

a strain carrying both a non-point cya mutation by deletion and a non-point crp mutation by deletion and denoted hereafter by the internal reference A; the strain C.N.C.M. I-529 is derived from this strain.

a strain not carrying any mutation capable of limiting or suppressing the expression of operons whose transcription can only be initiated after fixation of the cAMP-CRP complex, and known under the name MC1061 (*E. coli*, Genetic Stock Center, New-Haven, Conn., U.S.A.); this strain will be denoted hereafter by the internal reference T; the strain C.N.C.M. I-528 is derived from this strain.

Apart from the plasmid deposited in the C.N.C.M. under no. I-530, three other plasmids are mentioned in the examples: these are the plasmids denoted by the internal references p164,1, p200,3 and p212,6.

The plasmid p164,1 is very similar to the plasmid p163,1, the essential difference being the absence of the mutation UV5.

Figure 3:
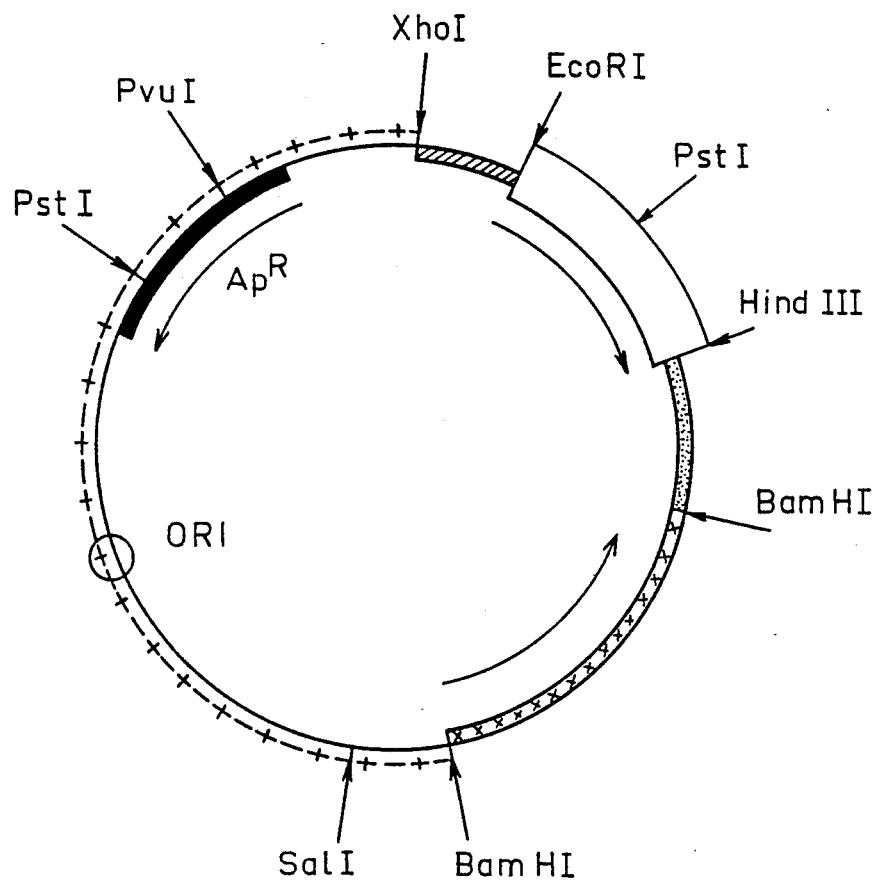

The plasmid p212,6 is similar to the plasmid p163,1. FIG. 3 represents a functional map thereof, showing the location and orientation of the main DNA which are represented symbolically according to the following legend, as depicted in FIG. 3a:

i. Origin of replication (ORI)
ii. DNA segment originating from the plasmid pBR327
iii. DNA segment containing the sequence coding for the natural precursor of hGH
iv. DNA segment of the phage fd containing a transcription terminator
v. DNA segment containing the gene Lac i and its promoter
vi. DNA segment containing the hybrid promoter-operator tryptophan-lactose UV5
vii. DNA segment coding for β-lactamase (ApR: ampicillin resistance)

As for the plasmid p163,1 shown in FIG. 2, the action sites of certain restriction enzymes are marked in FIG. 3.

The plasmid p200,3 is equivalent to the plasmid p212,6, chosen on account of its non-repressible character for the expression of the DNA sequence coding for the precursor of hGH.

The DNA sequence coding for one of the natural precursors of hGH and carried by the plasmids p212,6 and p200,3 differs from the sequence shown in FIG. 1 by two substitutions: the codon ACC has been substituted for the codon ACA coding for the amino acid located in the −24 position, and likewise the codon TCT has been substituted for the codon TCC coding for the amino acid located in the −22 position.

II. General methodology

The experiments performed consisted in cultivating the host-vector couples in question, prepared beforehand (cf. § 2.1), under conditions such that the host is capable of expressing the DNA sequence coding for the precursor of hGH (cf. § 2.2), expression being induced if necessary (cf. § 2.3), in collecting the proteins contained in the periplasmic space (cf. § 2.4) and in determining the periplasmic hGH (cf. § 2.5).

2.1. Preparation of the host-vector couples

The host-vector couples were prepared by the bacterial transformation techniques known to those skilled in the art and described especially in the following works:

—Molecular cloning—A Laboratory Manual, T. Maniatis, E. F. Fritsch and J. Sambrook, Cold Spring Harbor Laboratory, 1982.

Experiments in molecular genetics, J. H. MILLER, Cold Spring Harbor Laboratory, 1972.

2.2. Culture

(a) Inoculation

An isolated colony obtained on a solid medium (LB medium agar-agar) is suspended in 5 ml of a medium (LB medium), having the characteristics below, to which ampicillin has been added in a proportion of 100 µg/ml:

| | |
|---|---|
| base components introduced before autoclaving | 10 g |
| Pancreatic hydrolyzate of casein (Bactotryptone from DIFCO) | |
| Yeast extract | 5 g |
| Sodium chloride | 5 g |
| Distilled water ad | 1 l |
| pH adjusted to 7.3 before autoclaving | |

(b) Primary incubation 18 h at 37° C. so that the culture reaches the stationary growth phase.

(c) Dilution

The bacterial suspension is diluted in LB medium so as to give an optical density, read off at 600 nm– OD 600 nm—(Bausch-Lomb spectronic 20 spectrophotometer), of around 0.05.

(d) Secondary incubation 50 ml of the bacterial suspension obtained according to 2.2.c are incubated at 37° C. until the OD 600 nm is about 0.2.

2.3. Induction

Isopropyl-β-D-thiogalactose (or IPTG) is added to the bacterial suspension obtained according to 2.2.d in a quantity such that its final concentration is 1 mM; the IPTG is used here to initiate and sustain the synthesis of the precursor of hGH by neutralizing the action of the repressor which normally fixes to the lactose operator.

2.4. Osmotic shock (Reference may be made to the protocol described by N.G. NOSSAL and L.A. HEPPEL in "The Journal of Biological Chemistry 241 (1966) 3055-3062".)

(a) Preparation of the bacterial suspension

A sample of the suspension as obtained in 2.2.d (in cases where induction is not required), or as obtained after a given induction period, is taken and treated (centrifugation for 5 min at 6000 g, removal of the supernatant and resuspension of the bacteria in LB medium) so that it has an OD 600 nm of about 10.

(b) Washing

The suspension obtained in 2.4.a is centrifuged for 5 min at 6000 g.

The residue is taken up at constant volume in a solution A having the following composition: pH 7 buffer prepared by adding the following to distilled water:

tri(hydroxymethyl)aminomethane-HCl, or Tris-HCl, added so as to give a final concentration of 30 mM;

ethylenediaminetetraacetic acid, or EDTA, added so as to give a final concentration of 1 mM.

(c) Action of sucrose

The suspension obtained in 2.4.b is centrifuged for 5 min at 6000 g.

The residue is very carefully taken up at constant volume in a solution B corresponding to solution A to which sucrose is added in a proportion of 15 g per ml, and prepared for immediate use.

The suspension is left for 10 min at 20° C.

It is then centrifuged for 5 min at 6000 g.

The centrifuge tubes are placed in melting ice.

The supernatant is carefully removed and replaced (at constant volume) with deionized water kept at the temperature of melting ice.

The suspension prepared in this way (whose OD at 600 nm is about 10) is left for 5 min at 0° C.

(d) Collection of the proteins located in the periplasm

The suspension obtained in 2.4.c is centrifuged for 10 min at 18,000 g.

The supernatant is collected; it contains the proteins located in the periplasm.

2.5. Determination of the periplasmic hGH

(a) Methodology

The supernatant obtained in 2.4.d is subjected to a radioimmunoassay of the human growth hormone (COATRIAR ® $^{125}$I-hGH kit - Biomerieux, France).

This determination consists in carrying out the following in succession:

a reaction in which hGH labeled with iodine 125, introduced in a predetermined quantity, and the hGH contained in the analyzed sample to be determined compete for a first anti-hGH antibody in a predetermined quantity;

a reaction in which the first antibody is linked with a second antibody directed against the said first antibody and fixed to a solid substrate.

After incubation, the proportion of hGH labeled with iodine 125 is inversely proportional to the quantity of hGH in the sample to be determined.

2.6. Checking the nature of the periplasmic hGH

(1) Methodoloqy

The nature of the hGH, as collected from the supernatant obtained in 2.4.d, was checked.

This was done by carrying out the following operations in succession:

electrophoretic separation, on polyacrylamide gel, of the different proteins contained in the supernatant (in accordance with the protocol described by LAEMMLI - U.K. LAEMMLI, Nature 227 (1970) 680–685).

In this method, hGH in the mature form and the precursor of hGH migrate to two different points according to their respective apparent molecular weight.

transfer of the said proteins contained in the gel onto a nitrocellulose filter (in accordance with the technique of H. TOWBIN et al., Proc. Natl. Acad. Sci. U.S.A. SA 76 (1979) 4350–4354).

immunodetection performed in accordance with the technique of BURNETTE (W.W. BURNETTE, Anal. Biochem. 112 (1981) 195–203); it involves the following successive steps:
 rinsing the nitrocellulose filter for 10 min with a buffer A (Tris-HCl 10 mM, NaCl 170 mM, KI 1 mM);
 bringing the nitrocellulose filter into contact with a buffer B (buffer A to which bovine serum albumin has been added in a proportion of 3 g per 100 ml) for 30 min at 37° C.;
 bringing the nitrocellulose filter into contact with an immunoserum (a polyclonal antibody recognizing mature hGH and its precursor) for 18 h at 20° C.;
 rinsing the nitrocellulose filter with buffer B;
 bringing the nitrocellulose filter into contact, for 6 h at 20° C., with a solution of protein A labeled with 0.1 microcurie of iodine 125 per ml;
 rinsing the filter with buffer A;
 drying the filter between two absorbent sheets;
 bringing it into contact with an X-ray film; developing the film.

(2) Results

It was noted that, under the chosen operating conditions, the periplasmic hGH was present in its mature form in about 98% of the molecules, irrespective of the bacterial strain and plasmid used.

III. Results

3.1. Example A

Comparison of the levels of periplasmic hGH produced respectively by the host-vector couples *E. coli* strain T/p212,6 and *E. coli* C.N.C.M.I-528/p212,6.

With an induction time of 3 h 30 min, the following results were obtained:

| | Periplasmic hGH measured in micrograms per ml of supernatant collected after osmotic shock and adjusted to a turbidity such that OD 600 nm = 1 |
|---|---|
| Strain T/p212,6 | 0.86 |
| Strain C.N.C.M. I-528/p212,6 | 2.00 |

These results indicate that the mutant strain (strain C.N.C.M.I-528) is capable of producing periplasmic hGH more efficiently than the non-mutant strain (strain T), production being more than doubled.

3.2. Example B

Comparison of the levels of periplasmic hGH produced respectively by the host-vector couples *E. coli* strain T/p163,1, *E. coli* strain C.N.C.M.I-528/p163,1, *E. coli* strain T/p164,1 and *E. coli* strain C.N.C.M.I-528/p164,1.

With an induction time of 3 h, the following results were obtained:

| | Periplasmic hGH measured in nanograms per ml of supernatant collected after osmotic shock and adjusted to a turbidity such that OD 600 nm = 1 | |
|---|---|---|
| | p163,1 | p164,1 |
| Strain T | 5.8 | 6.4 |
| Strain C.N.C.M. I-528 | 7.8 | 10.8 |

The mutant strain (strain C.N.C.M.I-528) appears to be capable of producing periplasmic hGH in a significantly increased quantity (approx. 30% increase in one case and approx. 70% increase in the other case), whether or not the DNA sequence coding for the precursor of hGH is, for its expression, under the control of signals thought to be sensitive to the combined action of cAMP and CRP.

3.3. Example C

Comparison of the level of periplasmic hGH produced by the host-vector couples *E. coli* strain T/p200,3 and *E. coli* strainC.N.C.M.I-528/p200,3.

This experiment was performed without induction. The following results were obtained:

| | Periplasmic hGH measured in nanograms per ml of supernatant collected after osmotic shock and adjusted to a turbidity such that OD 600 nm = 1 |
|---|---|
| Strain T/p200,3 | 200 |
| Strain C.N.C.M. I-528/p200,3 | 512 |

The mutant strain (strain C.N.C.M.I-528) appears to be capable of producing periplasmic hGH more efficiently than the non-mutant strain (strain T), production being more than doubled.

This experiment shows that the effect obtained is of the same order whether or not the synthesis of the precursor is inducible.

3.4. Example D

Comparison of the level of periplasmic hGH produced by the host-vector couple *E. coli* strain NCMC I-529/p212,6, respectively in the presence and absence of cAMP.

With an induction time varying between 30 and 120 min, the following results were obtained:

| | Mature hGH in micrograms per ml of supernatant collected after osmotic shock and adjusted to a turbidity such that OD 600 nm = 1 | | |
|---|---|---|---|
| | After 30 min | After 60 min | After 120 min |
| In the absence of cAMP phenotype [cya⁻] | 0.153 | 0.670 | 1.650 |
| In the presence of cAMP phenotype | 0.100 | 0.243 | 0.975 |

| | Mature hGH in micrograms per ml of supernatant collected after osmotic shock and adjusted to a turbidity such that OD 600 nm = 1 | | |
|---|---|---|---|
| | After 30 min | After 60 min | After 120 min |
| [cya+]* | | | |

*In the presence of cAMP, the effects of the cya mutation are not expressed and the strain has a wild type [cya+]: it has the characteristics of a strain which has not undergone mutation for the cya character.

The mutant strain C.N.C.M.I-529 appears to be capable of producing periplasmic hGH more efficiently than a parent strain from which it only differs, under the chosen operating conditions, by the expression of a cya mutation.

3.5. Example E

Comparative measurements of the level of periplasmic hGH and the level of total periplasmic proteins produced by a given host-vector couple.

This experiment was performed with an induction time of 3 h.

The following results were obtained:

| Experimental conditions addition (+) or no addition (−) of cAMP and phenotype ( ) ( ) | (1) periplasmic hGH micrograms/ml | (2) total periplasmic proteins mg/ml | hGH/total periplasmic proteins $\frac{(1)}{(2) \times 10^3} \times 100$ |
|---|---|---|---|
| *1 + cAMP (cya+) (crp+) | 1 | 0.80 | 0.12% |
| *1 − cAMP (cya−) (crp+) | 3 | 0.37 | 0.81% |
| *2 + cAMP (cya+) (crp−) | 2.8 | 0.48 | 0.58% |

*1: strain C.N.C.M. I-529/p212, 6
*2: strain A/p212, 6

The periplasmic hGH values are expressed in micrograms per ml of supernatant collected after osmotic shock and adjusted to a turbidity such that OD 600 nm=1.

The total periplasmic proteins are measured by the method of BRADFORD (M. M. Bradford, Analytical Biochemistry 72 (1976) 248–264) and are expressed in mg per ml of supernatant collected after osmotic shock and adjusted to a turbidity such that OD 600 nm=1.

This experiment shows that the production of bacterial periplasmic enzymes in their mature form, assessed by measuring the level of proteins present in the periplasm, is reduced relative to the values obtained in the presence of a wild type strain and to a substantial extent in the presence of a strain whose chromosome carries a cya mutation (strain C.N.C.M.I-529 without exogenous addition of cAMP) or a crp mutation (strain A with exogenous addition of cAMP). At the same time, the production of periplasmic hGH is greatly increased when one or other of the mutations is expressed.

3.6. Example F

Comparison of the level of periplasmic hGH produced by the host-vector couples A/p212,6 and I-529/p212,6 in the absence of cAMP.

With an incubation time of 2 h, the following results were obtained:

| | Mature hGH in micrograms per ml of supernatant collected after osmotic shock and adjusted to a turbidity such that OD 600 nm = 1 |
|---|---|
| Strain A/p212,6 | 2.08 |
| Strain C.N.C.M.I-529/p212,6 | 2.07 |

It appears that the strain A whose chromosome carries a cya mutation by deletion and a crp mutation by deletion, and the strain I-529 whose chromosome carries the same cya mutation by deletion, are capable of identical performances.

These examples demonstrate the obvious advantage resulting from the use of strains carrying a mutation which limits, or even suppresses, the expression of the operons whose transcription can only be initiated after fixation of the cAMP-CRP complex: these strains in fact make it possible substantially to increase the production of the desired periplasmic protein (represented in these examples by 98% for the protein in its mature form). Example E also emphasizes the absolutely first-rate advantage afforded by the use of such bacteria: the increase observed is not only absolute but also relative, the mutant strains restricting the production of their own proteins normally located in the periplasm; this makes the target protein easier to purify from the contents of the periplasm.

What is claimed is:

1. A microbiological process for the preparation of a protein by culturing Gram-negative bacteria into which a DNA sequence coding for a precursor of this protein has been introduced, which comprises using a strain of bacteria whose chromosome carries at least one mutation affecting the system formed by the cya gene or the crp gene and the DNA sequences regulating expression of the cya gene or the crp gene, which mutation limits, or even suppresses, the expression of the operons whose transcription depends on the fixation of the cAMP-CRP complex, and wherein expression of the DNA sequence is not sensitive to the combined action of cAMP and CRP.

2. The microbiological process as claimed in claim 1, wherein the chromosome of the said bacteria carries at least one mutation affecting the system formed by the cya gene and the DNA sequences regulating its expression.

3. The microbiological process as claimed in claim 1, wherein the chromosome of the said bacteria carries at least one mutation affecting the system formed by the crp gene and the DNA sequences regulating its expression.

4. The microbiological process as claimed in claim 1, wherein the chromosome of the said bacteria carries at least one mutation affecting the system formed by the cya gene and the DNA sequences regulating its expression, and at least one mutation affecting the system formed by the crp gene and the DNA sequences regulating its expression.

5. The microbiological process as claimed in any one of claims 1 to 4, wherein the mutant bacterial strain used is a strain of the species *Escherichia coli*.

6. The microbiological process as claimed in claim 2, wherein the mutant bacterial strain has all the characteristics of the strain deposited in the C.N.C.M. under no. I-529.

7. The microbiological process as claimed in claim 3, wherein the mutant bacterial strain has all the characteristics of the strain deposited in the C.N.C.M. under no. I-528.

8. The microbiological process as claimed in claim 4 wherein the mutant bacterial strain is a strain of *Escherichia coli* whose chromosome carries two deletions, one of which affects the system formed by the cya gene and the DNA sequence regulating its expression, the other affecting the system formed by the crp gene and the DNA sequences regulating its expression.

9. The microbiological process as claimed in claim 1, wherein the DNA sequence coding for the precursor of the desired protein, accompanied by the regulator elements permitting its expression, is carried by a plasmid.

10. The microbiological process as claimed in claim 1, wherein the said bacterial strain contains a DNA sequence coding for a precursor of human growth hormone.

11. The microbiological process as claimed in claim 10, wherein the said DNA sequence is carried by a plasmid having all the characteristics of the plasmid deposited in the C.N.C.M. under no. I-530.

12. The microbiological process as claimed in claim 1 wherein the mutant bacterial strain is *Escherichia coli* and the presence of a promoter bearing the mutation UV5 renders expression of the DNA sequence insensitive the combined action of cAMP and CRP.

13. The microbiological process as claimed in claim 1 wherein the mutant bacterial strain is *Escherichia coli* and the expression of the DNA sequence is placed under the control of a hybrid promoter-operator associating a fragment of the tryptophan promoter starting from its 5' end and including its RNA polymerase recognition site, and the promoter-operator lactose UV5 without its 5' terminal portion and its RNA polymerase recognition site.

14. A bacterial strain having all the characteristics of the strain deposited in the C.N.C.M under no. I-528.

15. A bacterial strain having all the characteristics of the strain deposited in the C.N.C.M. under no. I-529.

* * * * *

UNITED STATES PATENT AND TRADEMARK OFFICE
CERTIFICATE OF CORRECTION

PATENT NO. : 4,945,047
DATED : 7/31/90
INVENTOR(S) : Legoux, et al.

It is certified that error appears in the above—identified patent and that said Letters Patent is hereby corrected as shown below:

Column 6, line 38, should recite:
"main DNA sequences, which"

Column 7, line 26, should recite:
"medium + agar-agar"

Column 8, line 26, should recite:
"15g per 100ml"

Signed and Sealed this

Eighth Day of September, 1992

Attest:

DOUGLAS B. COMER

Attesting Officer

Acting Commissioner of Patents and Trademarks